United States Patent
Levadoux et al.

(10) Patent No.: US 11,668,703 B2
(45) Date of Patent: Jun. 6, 2023

(54) METHOD FOR DETERMINING THE LEVEL OF ZYGOSITY OF A SEED

(71) Applicant: BIOGEMMA, Chappes (FR)

(72) Inventors: Sylvain Levadoux, Clermont-Ferrand (FR); Thierry Risacher, Clermont-Ferrand (FR)

(73) Assignee: LIMAGRAIN EUROPE, Saint Beauzire (FR)

( * ) Notice: Subject to any disclaimer, the term of this patent is extended or adjusted under 35 U.S.C. 154(b) by 737 days.

(21) Appl. No.: 16/490,368

(22) PCT Filed: Mar. 23, 2018

(86) PCT No.: PCT/EP2018/057441
§ 371 (c)(1),
(2) Date: Aug. 30, 2019

(87) PCT Pub. No.: WO2018/172522
PCT Pub. Date: Sep. 27, 2018

(65) Prior Publication Data
US 2020/0072818 A1    Mar. 5, 2020

(30) Foreign Application Priority Data
Mar. 24, 2017 (EP) .................................. 17305341

(51) Int. Cl.
G01N 33/50 (2006.01)
C12Q 1/686 (2018.01)
G01N 1/28 (2006.01)
G01N 21/64 (2006.01)

(52) U.S. Cl.
CPC ......... *G01N 33/5097* (2013.01); *C12Q 1/686* (2013.01); *G01N 1/28* (2013.01); *G01N 21/6486* (2013.01)

(58) Field of Classification Search
None
See application file for complete search history.

(56) References Cited

U.S. PATENT DOCUMENTS

2016/0355894 A9 * 12/2016 Ren ...................... C12Q 1/6895

OTHER PUBLICATIONS

International Search Report and Written Opinion dated Jul. 2, 2018, for corresponding PCT Application No. PCT/EP2018/057441.
Hensel, G. et al., "Transgenic Production of an Anti HIV Antibody in the Barley Endosperm", PLOS ONE; vol. 10; No. 10; 2015; pp. 1-18.
Shimada, T. et al., "A rapid and non-destructive screenable marker, FAST, for identifying transformed seeds of *Arabidopsis thaliana*", The Plant Journal; vol. 61; No. 3; 2010; pp. 519-528.
Rademacher, T. et al., "Recombinant antibody 2G12 produced in maize endosperm efficiently neutralizes HIV-1 and contains predominantly single-GlcNAc N-glycans", Plant Biotechnology Journal; vol. 6; No. 2; 2008; pp. 189-201.
Shimada, T. et al., "A non-destructive screenable marker, OsFAST, for identifying transgenic rice seeds", Plant Signaling & Behavior; vol. 6; No. 10; 2011; pp. 1454-1456.
Carlson, A. R. et al., "Visual screening of microspore-derived transgenic barley (Hordeum vulgare L.) with green-fluorescent protein" Plant Cell Reports; vol. 20; No. 4; 2001; pp. 331-337.
Richards, H. A. et al., "Quantitative GFP fluorescence as an indicator of recombinant protein synthesis in transgenic plants", Plant Cell Reports; vol. 22, No. 2; 2003; pp. 117-121.
Molinier, J. et al., "Use of green fluorescent protein for detection of transformed shoots and homozygous offspring", Plant Cell Reports; vol. 19; No. 3; 1999; pp. 219-223.

* cited by examiner

*Primary Examiner* — Medina A Ibrahim
(74) *Attorney, Agent, or Firm* — Polsinelli PC

(57) ABSTRACT

The invention relates to a method for determining the level of transgene zygosity in a *poaceae* seed, the transgene being genetically linked to a gene coding for a fluorescent protein (FP protein) under the control of a promoter operative in the endosperm, comprising the step of exposing the endosperm of the seed to a wavelength exciting the FP protein, and measuring the intensity of the emitted fluorescence.

12 Claims, 7 Drawing Sheets
Specification includes a Sequence Listing.

a.  b.

SEQUENCE LISTING

```
<160> NUMBER OF SEQ ID NOS: 6

<210> SEQ ID NO 1
<211> LENGTH: 1249
<212> TYPE: DNA
<213> ORGANISM: Artificial Sequence
<220> FEATURE:
<223> OTHER INFORMATION: HMWG promoter from wheat from GenBank AJ301618

<400> SEQUENCE: 1
gcatgcaaat atgcaacata atttccttt tacttggcta attatatttg ataaatattt      60
cacagatata caataatcaa acacaataaa tcatatgtgt ttttagtttt agttctcata    120
tccaaatata caatagctaa ccaaatctca tcgggaagtt agccatgccg aggtaggttg    180
ttgccggaat gtttttagtt ttagttctca tacaaccaaa tctcattcaa atatataaaa    240
cattccggca acaacttgtg gcgtacatct agttacaagg gaatattagt gatggcgtga    300
gcaagcgata aggccaagga gagaagaagt gcatcgtcta cggaggccag ggaaagacaa    360
tggacatgca gagaggcagg ggcggggaag aaacacttgg agatcataga agaagataag    420
aggttaaaca taggaggagg atataatgga caattaaatc tgcgttagtt gaactcattt    480
gggaagtaaa caaattttct attctgtgta aaccaaacta tttgacgcgg attttctctg    540
aagatcctat attaatttta gacatggttt ggctagttca tttgtcgtga aaaggtgttt    600
ccataagtcc aaaattctac caacttttt gtatggcacg tcatagcata gatagatgtt    660
gtgagtcact ggatagatat tgtgagtcat agcatggatt cgtgttgctg gaaatccaac    720
tacatgacaa gcaacaaaac ctgaaatggg ctttaggagt taacaattta cttgttccat    780
gcaggctacc ttccactact cgacatgctt agaagctttg agtggccgta gatttgcaaa    840
agcaatggct aacagacaca tattctgcca aaccccaaga aggataatca cttttcttag    900 ataaaaaga acagaccaat atacaaacat ccacacttct gcaaacaata catcagaact    960
aggattacgc cgattacgtg gctttagcag actgtccaaa aatctgtttt gcaaagctcc   1020
aattgctcct tgcttatcca gcttcttttg tgttggcaaa ctgcgcttt ccaaccgatt   1080 ttgttcttct cgcgctttct tcttaggcta aacaaacctc accgtgcacg cagccatggt   1140
cctgaacctt cacctcgtcc ctataaaagc ctagccaacc ttcacaatct tatcatcacc   1200
cacaacaccg agcaccacaa actagagatc aattcactga tagtccacc                1249
```

<210> SEQ ID NO 2
<211> LENGTH: 417
<212> TYPE: DNA
<213> ORGANISM: Artificial Sequence
<220> FEATURE:
<223> OTHER INFORMATION: promoter HMWG of wheat (Triticum aestivum),
      bases 814 to 1220 of SEQ ID NO: 1

<400> SEQUENCE: 2

```
agctttgagt ggccgtagat ttgcaaaagc aatggctaac agacacatat tctgccaaac    60
cccaagaagg ataatcactt ttcttagata aaaaagaaca gaccaatata caaacatcca   120
cacttctgca aacaatacat cagaactagg attacgccga ttacgtggct ttagcagact   180
gtccaaaaat ctgttttgca aagctccaat tgctccttgc ttatccagct tcttttgtgt   240
tggcaaactg cgcttttcca accgattttg ttcttctcgc gctttcttct tagcctaaac   300
aaacctcacc gtgcacgcag ccatggtcct gaaccttcac ctcgtcccta taaaagccta   360
gccaaccttc acaatcttat catcacccac aacaccgagc accacaaact agagatc     417
```

<210> SEQ ID NO 3
<211> LENGTH: 696
<212> TYPE: DNA
<213> ORGANISM: Artificial Sequence
<220> FEATURE:
<223> OTHER INFORMATION: ZsGreen_ZmMod Fluorescent protein coding
      sequence

<400> SEQUENCE: 3

```
atggctcagt caaagcacgg gctcacaaag gagatgacta tgaagtacag gatggagggc    60
tgcgtcgatg ggcacaagtt cgttatcacc ggcgagggga tcggctaccc gttcaagggc   120
aagcaggcga ttaacctgtg cgtggtcgag ggcgggccac tgcccttcgc tgaggatatc   180
ctctccgccg cgttcatgta cggcaacagg gttttcaccg agtacccgca ggacattgtc   240
gattacttca gaattcctg cccagctggg tacacgtggg acaggagctt cctcttcgag   300
gatggcgctg tgtgcatctg caacgccgac attaccgttt cggtggagga gaattgcatg   360
taccacgagt ctaagttcta cggggtgaac ttcccagctg acggcccgt catgaagaag   420 atgacggata ttgggagcc atcatgcgag aagatcattc cagtgcctaa gcagggatc   480 ctgaagggcg acgtctccat gtacctcctg ctcaaggatg gcggcaggct caggtgccag   540
ttcgacacag tctacaaggc caagagcgtt ccacgcaaga tgcctgactg cacttcatc   600 cagcataagc tgactcggga ggaccgctcg gatgcgaaga accagaagtg gcacctgact   660
gagcacgcta tcgcctcggg gtccgccctc ccttga                             696
```

<210> SEQ ID NO 4
<211> LENGTH: 720
<212> TYPE: DNA
<213> ORGANISM: Artificial Sequence
<220> FEATURE:
<223> OTHER INFORMATION: Fluorescent protein coding sequence derived
      from Aequorea victoria

<400> SEQUENCE: 4

```
atggtgagca agggcgagga gctgttcacc ggggtggtgc ccatcctggt cgagctggac    60
ggcgacgtga acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca cctttcaccta cggcgtgcag tgcttcagcc gctaccccga ccacatgaag   240
```

```
cagcacgact tcttcaagtc cgccatgccc gaaggctacg tccaggagcg caccatcagc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca ccgccgacaa gcagaagaac      480
ggcatcaagg ccaacttcaa gatccgccac aacgtcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720
```

<210> SEQ ID NO 5
<211> LENGTH: 1363
<212> TYPE: DNA
<213> ORGANISM: Artificial Sequence
<220> FEATURE:
<223> OTHER INFORMATION: Construct proTaHMWG - ZsGreen_ZmMod - terAtNOS

<400> SEQUENCE: 5

```
agctttgagt ggccgtagat ttgcaaaagc aatggctaac agacacatat tctgccaaac       60
cccaagaagg ataatcactt ttcttagata aaaagaaca gaccaatata caaacatcca      120
cacttctgca aacaatacat cagaactagg attacgccga ttacgtggct ttagcagact      180
gtccaaaaat ctgttttgca aagctccaat tgctccttgc ttatccagct tcttttgtgt      240
tggcaaactg cgcttttcca accgattttg ttcttctcgc gctttcttct tagcctaaac      300
aaacctcacc gtgcacgcag ccatggtcct gaaccttcac ctcgtcccta taaaagccta      360
gccaaccttc acaatcttat catcacccac aacaccgagc accacaaact agagatcatg      420
gctcagtcaa agcacgggct cacaaaggag atgactatga agtacaggat ggagggctgc      480
gtcgatgggc acaagttcgt tatcaccggc gaggggatcg gctacccgtt caagggcaag      540
caggcgatta acctgtgcgt ggtcgagggc gggccactgc ccttcgctga ggatatcctc      600
tccgccgcgt tcatgtacgg caacaggatt ttcaccgagt acccgcagga cattgtcgat      660
tacttcaaga attcctgccc agctgggtac acgtgggaca ggagcttcct cttcgaggat      720
ggcgctgtgt gcatctgcaa cgccgacatt accgtttcgg tggaggagaa ttgcatgtac      780
cacgagtcta agtcctacgg ggtgaacttc ccagctgacg gccccgtcat gaagaagatg      840
acggataatt gggagccatc atgcgagaag atcattccag tgcctaagca ggggatcctg      900
aagggcgacg tctccatgta cctcctgctc aaggatggcg gcaggctcag gtgccagttc      960
gacacagtct acaaggccaa gagcgttcca cgcaagatgc ctgactggca cttcatccag     1020
cataagctga ctcgggagga ccgctcggat gcgaagaacc agaagtggca cctgactgag     1080
cacgctatcg cctcggggtc cgccctccct tgagatcgtt caaacatttg gcaataaagt     1140
ttcttaagat tgaatcctgt tgccggtctt gcgatgatta tcatataatt tctgttgaat     1200
tacgttaagc atgtaataat taacatgtaa tgcatgacgt tatttatgag atgggttttt     1260
atgattagag tcccgcaatt atacatttaa tacgcgatag aaaacaaaat atagcgcgca     1320
aactaggata aattatcgcg cgcggtgtca tctatgttac tag                      1363
```

<210> SEQ ID NO 6
<211> LENGTH: 250
<212> TYPE: DNA
<213> ORGANISM: Artificial Sequence
<220> FEATURE:

```
<223> OTHER INFORMATION: Nopaline synthase (NOS) terminator from
      Arabidopsis thaliana

<400> SEQUENCE: 6
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggtttttatg attagagtcc cgcaattata catttaatac     180
gcgatagaaa acaaaatata gcgcgcaaac taggataaat tatcgcgcgc ggtgtcatct     240
atgttactag                                                            250
```

METHOD FOR DETERMINING THE LEVEL OF ZYGOSITY OF A SEED

CROSS-REFERENCE TO RELATED APPLICATIONS

This application is a national stage application (under 35 U.S.C. § 371) of PCT/EP2018/057441, filed Mar. 23, 2018, which claims benefit of European Application No. 17305341.4, filed Mar. 24, 2017, which are incorporated herein by reference in their entireties.

The invention is used in the field of breeding and relates to a method to determine the level of zygosity (ploidy) of a transgene in a seed, making it possible to detect and select seeds that can be further used in breeding programs.

BACKGROUND OF THE INVENTION

Plant transformation with transgene is now a widely used technique and makes it possible to obtain plants presenting a phenotype (trait) that is absent from wild-type plants. One can introduce transgenes that are exogenous/heterologous to the plants (such as herbicide resistance transgenes or microbial toxins to obtain resistance to pests) or genes that are already present in the wild-type plant, but under the control of specific promoters so as to promote expression of the transgene in specific tissues (such as roots, leafs, or different tissues within or around the embryo) or at specific period of times (such as during growth of the embryo or at the flowering time) or in response to specific stresses (such as abiotic (such as extreme temperatures, drought, flood, lack of or low nitrogen . . . ) or biotic (such as attack of pests such as bacteria, viruses, fungi, parasites,) stresses).

This technique opens wide opportunities to get improved plants but a limited number of transgenic plants has been effectively led to the market. The selection of the valuable transgenic events is a main step for the companies working on this technology. The choice of a candidate gene for a specific species, the use of this gene for transgenesis by overexpression, RNAi or another approach, the choice of the appropriate promoter: constitutive, tissue or development specific, time, stress, inducer or reagent inducible, with low, medium or higher rate of expression, the choice of terminator and others regulative elements can be validate by a first proof of concept step. A great number of transgenic candidate are produced at this step to select the correct combination to be use for transgenic events. This can include a combination of candidate genes.

Plants are generally transformed with a vector containing the transgene(s) of interest, using any method known in the art, such as the *Agrobacterium* transformation method. Generally, the varieties that are used for transformation are plants that are specifically adapted for this purpose, and transgenes need to be transferred via introgression in commercially interesting plants, having a genetic background adapted for the sought commercial business, for future evaluation.

The transformation leads to a plant named "T0", which is able to give a limited number of seeds. These T0 plants can't be used for phenotypical evaluation due to the high rate of variability of the plants used for transformation and the in vitro origin of these plants. After regeneration, selection of plant on the copy number of the transgene, and self-fertilization, the repartition of the seeds obtained, from T0 plants with one copy number, is ¼ seeds homozygous for the transgene, ½ seeds heterozygous and ¼ seeds which don't carry the transgene. A first evaluation of the trait induced by the transgenic construct can be done on the plants from this step, by comparison of homozygous and heterozygous plants from the transgenes to the control plants from the cross containing no transgene.

Moreover the best characterization is preferably done after crossing of the transgenic plant with a line to have a more appropriate genetic background.

In order to speed up processes, it is preferred to use homozygous seeds for this cross to obtain a hybrid progeny heterozygous for the transgene. Previously, the seeds were sown and qPCR was performed to identify the plants for which the progeny was to be kept and further used. However, this is time and space consuming and there is a need to provide a method that is more simple and quicker to determine the level of ploidy of seeds, which will then make it possible to keep the interesting one and discard the others.

The use of Fluorescent proteins (FP) appeared in the transgenic strategies, during the 1990's, mainly as selectable markers to follow transgenic events. GFP for Green Fluorescent Protein isolate from jellyfish *Aequorea victoria* is the most known of these protein, and the initial protein has been successively modified to be more easily visualized.

Fluorescent protein is also widely used for promoter evaluation.

Stewart et al (2001) have shown that it is possible to use GFP as a visual selectable marker in aiding the plant transformation process, for nuclear or plasmid transformation. Quantification of GFP expression is possible and makes it possible to assess the concentration of proteins of interest genetically linked to this marker gene (Halfhill et al., 2004). The quantification of fluorescence requires the use of various tools such as spectrofluorometers or fluorescence imaging systems (Niwa et al, 1999, Halfhill et al., 2004). Using these tools, some authors have shown a correlation between the intensity of GFP and the level of zygosity of the measured sample (Niwa et al., 1999, Molinier et al., 2000). Indeed, upon observation and quantification of fluorescence on leaves or seedlings from T2 generation, the intensity of GFP can separate homozygous, which have a fluorescence twice more intense than hemizygotes (Niwa et al., 1999, Molinier et al., 2000). In particular, Molinier describes the division of tobacco seeds in three classes (high, low, and no fluorescence) according to their level of GFP fluorescence.

The use of GFP has been recently described in the field of double haploid method for maize, an inducer line containing the GFP marker has been create by Yu and Birchler 2016: the RWS-GFP line. When a line is crossed by this inducer line, haploid seeds are fluorescent on the endosperm and have no fluorescence of the embryo. The author's mentions that screening of haploid seed on dry kernels is possible but that it is easier to screen haploid after germination of the seeds; in this cross the fluorescence of the endosperm is linked to the copy of the fluorescent protein from the inducer line, the screening is simply done for seed with or without the Fluorescent protein.

Hensel et al (PLOS ONE, vol. 10, no. 10, 2015, page e0140476) discloses use of transgenic barley to produce an anti-HIV-1 monoclonal antibody in the endosperm. Production of recombinant GFP in the endosperm is also reported. This document is not concerned by the determination of the zygosity of plants by measure of fluorescence.

Shimada et al (The Plant Journal, vol. 61, no. 3, 2010, pages 519-528) discloses expression of a fluorescent co-dominant screenable marker FAST, under the control of a seed-specific promoter, on the oil body membrane in *Arabidopsis thaliana*, and the possibility to discriminate between homozygous and heterozygous plants. It is however to be noted that *Arabidopsis* plants don't present double fertilization as angiosperm plants.

Rademacher et al (Plant Biotechnology Jou, vol. 6, no. 2, 2008, pages 189-201) discloses expression of an antibody in the endosperm of maize, together with the fluorescent marker protein Discosoma red fluorescent protein (DsRed), which helps to identify antibody-expressing lines and trace transgenic offspring when bred into elite maize germplasm, GFP is observed on pollen and segregation on ears. The GFP marker is not suggested nor described for determination of the zigosity of the plants into the endosperm.

Shimada et al (Plant Signaling & Behavior 6:10 1454-1456; October 2011) disclose use of a non-destructive screenable marker, OsFAST, expressed in rice embryos, for identifying transgenic rice seeds.

Carlson et al (Plant Cell Reports, June 2001, Volume 20, Issue 4, pp 331-337) discloses use of the GFP as a screenable marker in the production of transgenic barley plants under the control of an ubiquitous promoter, visualization of GFP is done on pollen and roots.

Richards et al (Plant Cell Rep. 2003 September; 22(2): 117-21) disclose measurement of the levels of GFP expression in leaves of homozygous and hemizygous plants.

However, none of these documents describe the use of a fluorescent protein in combination with a promoter i.e. able to promote expression of a gene, in the endosperm of the plant, (and preferably specific of the endosperm) to detect FP expression in this organ of the plant and being able to determine the ploidy (zygosity) of a transgene in the plant, and the use in angiosperm plants (in particular poaceae or gramineae plants), where there is presence of four classes of seeds (0×, 1×, 2× and 3× copies of the transgene). In particular, the promoter used to drive the FP expression can be a constitutive promoter or an endosperm-specific promoter.

In certain species (e.g. corn, *Zea mays*), the storage function is distributed between both endosperm and the embryo. Some mature endosperm tissue stores fats (e.g. castor bean, *Ricinis communis*) and others (including grains, such as wheat and corn) store mainly starches.

Quantification of the fluorescence of the FP gene on caryopses of maize is indicative of the level of zygosity of the fluorescent protein, and hence of the transgene, in the seed, in particular when the FP gene is expressed under control of the HMWG promoter, which is specific of albumen (Thomas et al., 1990). This promoter naturally controls expression of prolamines, which are plant storage proteins, and will thus lead expression of the FP only on the part of the caryopse that correspond to starch reserves (Lamacchia et al., 2001). The HMWG promoter, being specific of the endosperm, makes it possible to observe and study the fluorescence (indicative of the presence and number of transgene) directly on the seed, without the need to sow the seeds. Furthermore, the solution herein proposed make it possible to discriminate, in angiosperm plants, between homozygous plants having three copies of the transgene (and of the FP) and hemizygous plants having only one or two copies of the transgene in the endosperm. It thus makes it possible to conclude about the number of copies of the transgene in the embryo. As indicated below, due to the double fertilization of Angiosperm plants, the endosperm can contain form 0 to 3 copies of the transgene.

It is also to be noted that the method disclosed herein below can be easily automated, while it is more difficult to automate a method that detects fluorescence directly on the embryo. Indeed, the embryo may be difficult to identify, and is generally quite small with regards to the size of the whole seed. If the measure was to be made on the embryo, there would thus be a risk not to be specific enough and to also measure fluorescence of the endosperm. The result and conclusion may thus be erroneous for angiosperm plants, due to the double fertilization in these plants. Consequently, in these plants, measuring a high fluorescence doesn't necessarily mean that the embryo is 2×.

The solution proposed in the present application is to genetically link the transgene to a FP (Fluorescent Protein) gene, to detect and quantify the emission of the fluorescence of the FP in the endosperm of the seed. The FP is thus under the control of a promoter active in the endosperm, and preferably specific of the endosperm.

This method is of particular interest in angiosperm plants (*Angiospermae* or *Magnoliophyta*), as it also makes it possible to determine whether the embryo is homozygous (which is what is important), as there are three copies of genomes in the seed (in the endosperm).

Angiosperms indeed present the phenomenon of double fertilization.

This refers to a process in which two sperm cells fertilize cells in the ovary. A pollen grain adheres to the stigma of the pistil (female reproductive structure), germinates, and grows a pollen tube. A haploid (n chromosomes) generative cell travels down the tube behind the tube nucleus, and divides by mitosis to produce two haploid (n) sperm cells. The pollen tube grows and makes its way from the stigma, down the style and into the ovary, to reach the micropyle of the ovule and digest its way into one of the synergids, releasing its contents (in particular the two sperm cells). The synergid then will degenerate and one sperm will fertilize the egg cell, producing a diploid (2n) zygote. The second sperm cell fuses with both central cell nuclei of the large central cell of the megagametophyte, producing a triploid (3n) cell. As the diploid zygote develops into the embryo, the triploid cell develops into the endosperm, which serves as the embryo's food supply.

The ovary, surrounding the ovules, develops into the fruit, which protects the seeds and may function to disperse them.

One can note that the two central cell maternal nuclei (polar or central nuclei) contributing to the endosperm, arise by mitosis from the same single meiotic product that gave rise to the egg. Consequently, the maternal contribution to the genetic constitution of the triploid endosperm is double that of the embryo (two series of chromosomes come are from maternal origin and one set of chromosomes is from paternal origin).

Depending on the level of the detected fluorescence in the endosperm it will make it possible to conclude that there is
- 0 copy (0×) of the transgene in the endosperm (and hence of the FP protein). In any case, the embryo is wild type
- 1 copy (1×) of the transgene in the endosperm: the copy comes from the male gamete. In any case, the embryo will be heterozygous (hemizygous) for the transgene
- 2 copies (2×) of the transgene in the endosperm: the copies come from the female gamete. In this case, the embryo would be heterozygous for the transgene.
- 3 copies (3×) of the transgene in the endosperm: the copies come from both the male and female gametes. In this case, the embryo is thus homozygous for the transgene.

The invention thus relates to a method for determining the level of transgene zygosity (or ploidy) in a seed, in particular an Angiosperm seed and most preferably a *Poaceae* (*Gramineae*) seed, wherein said transgene is genetically linked to a FP gene under the control of a promoter active in the endosperm, in particular an endosperm specific-promoter, comprising the step of exposing the endosperm of the seed to a wavelength exciting the FP protein, and measuring the intensity of the emitted fluorescence.

Due to the fact that seeds have a translucent or semi-translucent seed coat, it is thus easy to detect the fluorescent, measure the level thereof and classify the seeds in various classes, as exemplified below.

Transgene zygosity or ploidy is intended to mean the number of copies of the transgene in the genome of the seed studied.

Since the fluorescent protein is genetically linked to the transgene, the intensity of emitted fluorescence is directly linked of the level of transgene zygosity. It is thus an indicator of the transgene zygosity, as indicated above.

In one embodiment, the intensity of emitted fluorescence is calculated after processing of the image of the seed in a computer. In a preferred embodiment, one will use a plate reading fluorimeter.

In particular, when the seed is irradiated with the filtered light, the FP expressed in the seed is excited and emits fluorescent light.

The image of the seed can be visualized in a photograph. In this regard, a CCD color camera can be used. It is preferably a high-resolution color camera and can be equipped with a zoom lens. The camera is positioned on the axis vertical to the plane of the seed to take a photograph of the seed while focusing on the endosperm of the seed with the zoom lens.

When the Green Fluorescent Protein (see below) is used, the light emitted from the FP has a wavelength of about 509 nm. It is thus preferred when a bandpass filter for passing the green light ranging in wavelength from 500 to 550 nm is placed in front of the CCD camera to pass the green fluorescent light only. The images captured by the CCD camera are then sent to a computer in which the image data are collected, stored and processed. Measure of the intensity of the fluorescence is performed as described below.

The wavelength emitted to excite the protein and the band pass filter are easily adapted if other Fluorescent Proteins are used.

In order to determine the ploidy of the seed, it is preferred when the intensity of the emitted fluorescence is compared with the intensity of fluorescence of controls, such as the intensity of fluorescence that has been previously emitted for the endosperm of seeds that are haploid, diploid or triploid for the FP under the control of said promoter active in the endosperm. The intensity of the emitted fluorescence of this seed is then compared with the intensity of fluorescence that has been previously emitted for seeds having 0×, 1×, 2× or 3× copies of the gene coding for the FP under the control of said promoter.

It is also possible to use control seeds that are 0×, 1×, 2× or 3× for the FP under the control of said endosperm specific-promoter during the experiment when the sample seeds are tested. In this embodiment, control seeds are also exposed to said wavelength exciting the FP protein, wherein the intensity of the emitted fluorescence is measured for said control seeds and compared with the intensity of the emitted fluorescence for said seed bearing the transgene and the FP. Preferably these controls originate from the same transformation event than the tested seeds.

In another embodiment, the measure is performed on batches of seeds or seed lots, meaning that seed have the same origin progeny from the same plant (self-pollination) or from the same transgenic event, and the seeds are classified according to the class to which they belong, using the fact that they should statistically be equally allocated in each class (classes are thus determined intra-lot). As indicated in the examples, this kind of analysis doesn't necessitate prior knowledge of the fluorescence intensity level or use of control seeds, and can be performed using software available in the art.

By "genetically linked" it is intended to mean that the transgene and the FP gene do not segregate from each other in subsequent generations so that presence of one gene is indicative of the presence of the other gene. This may be easily obtained during the preparation of the vector used for the transformation, by placing the FP gene (including the endosperm-specific promoter, coding sequence, terminator and any other sequence such as an enhancer sequence or the like) a few bases upstream (in the 5' end) or downstream (in the 3' end) of the transgene sequence (which include the transgene promoter, transgene coding sequence, terminator and any other sequence such as an enhancer sequence or the like.

Thus, when preparing the vector before *Agrobacterium* or direct (such as bombardment) transformation, the genes are contained in the same T-DNA (in case of *Agrobacterium* transformation method) or on the same plasmid DNA or plasmid fragment (in case of direct transformation method). It is to be noted that when co-transformation or bombardment methods are used, the sites of integration of the transgene and the FP are linked in the majority of the cases. This can easily be checked by methods known in the art.

The FP coding sequence is under the control of a promoter that is functional (i.e. that is capable of driving expression of the gene) in the endosperm.

A promoter "functional in a given tissue" of a plant is a promoter that allows expression of a nucleic acid sequence operatively linked to it in said given tissue of said plant.

In a preferred embodiment, said promoter is predominantly functional in the endosperm, i.e. said promoter can be active in other tissues than the endosperm, but the principal expression of a nucleic acid sequence encoding a protein operatively linked to it is in the endosperm. This can be verified, using various techniques known by the person skilled in the art, such as quantification of the RNA expression of said nucleic acid sequence in various tissues by Northern blot, or of the protein expression in various tissues by Western blot. After quantification of the mRNA of the gene in the whole seed, mRNA quantity in the endosperm amounts to 80%, more preferably 90% or more of the total mRNA quantified.

The promoter can be specific to the endosperm. A promoter specific to a given tissue is active exclusively in said tissue, i.e. it is not possible to detect expression of a nucleic acid sequence encoding a protein operatively linked to it in other tissues than said given tissue, by the techniques listed above.

In a preferred embodiment, said promoter is chosen in the group consisting of: the proZmgZein (gamma Zein) (Russel and Fromm Transgenic Res. 1997 March; 6(2):157-68; the gene sequence is available at Genebank X53514)

the CaMV35S promoter (Odell et al, Nature. 1985 313: 810-812; GenBank E05206, JP 1993192172), alone or with the *Zea mays* alcohol dehydrogenase gene, intron 1 (int1ZmAdh1, GenBank AY241178)

the rice actin promoter, alone or with the first rice actin intron proOsActin1-intOsActin1 (McElroy et al 1990, Plant Cell 2:163; Genebank: X63830)

the maize polyubiquitin promoter (proZmUbi1), alone or in combination with the first intron (proZmUbi1-intZmUbi1) as depicted in GenBank S94464 and in Christensen et al, Plant Mol. Biol. 18 (4), 675-689 (1992)

the rice tubulin promoter proOsTubA-intOsTubA (Fiume et al. Planta. 2004 March; 218(5):693-703)

the CsVMV promoter, as described in Verdaguer et al, Plant Mol. Biol. 31 (1996) 1129-1139, alone or with the first intron of the rice Actin gene (Vain et al, 1996, Plant Cell Reports 15: 489-494 and GenBank X63830)

In the preferred embodiment, said promoter is the HMWG promoter, described in Halford et al 1989 (Plant Science 62, 207-16) having sequence SEQ ID NO: 1, depicted under accession number AJ301618 or a shorter version as depicted in SEQ ID NO: 2.

It is reminded that the green fluorescent protein (GFP) is a protein composed of 238 amino acid residues (26.9 kDa) that exhibits bright green fluorescence when exposed to light in the blue to ultraviolet range. This protein is well known in the art. The first isolated GFP protein was from the jellyfish *Aequorea Victoria*, and presents has a major excitation peak at a wavelength of 395 nm and a minor one at 475 nm with an emission peak is at 509 nm The GFP from the sea pansy (*Renilla reniformis*) has a single major excitation peak at 498 nm.

Multiple derivatives have been designed (such as EGFP (enhanced, point mutation F64L), CFP (Cyan), EYFP (yellow) and its variants Venus and Citrine, EBFP (blue) and its variant Azurite, PA-GFP (which can be activated at 405 nm), PHluorin).

Couples excitation/emission wavelengths are provided below (in nm):
ECFP 433/475
mCherry 587/610
ZsGreen 493/505
ZsYellow 529/539
AmCyan 458/489
DsRed2 563/582
E2-Crimson 611/646

One can also refer to EP 1 135 532 B1 and Matz, M. V. et al. (1999) Nature Biotechnol. 17(10): 969-973, and to documents cited in the reference list.

One can also see a list of such proteins, for instance on https://en.wikipedia.org/wiki/Green_fluorescent_protein#GFP_derivatives.

Other fluorescent proteins exist in nature or have been designed though genetic engineering. A list of these (such as dsRed, eqFP611, Dronpa, TagRFPs, KFP, EosFP, Dendra, IrisFP) may be found at https://en.wikipedia.org/wiki/Green_fluorescent_protein In the context of the invention, a GFP protein is a protein that is able to emit a detectable radiation at a specific wavelength, upon excitation by a radiation at another specific wavelength, as does the *A. Victoria* GFP at 509 nm and 395 nm (or 475 nm) respectively.

In particular, the FP protein used in the context of the invention may be the ZsGreen from *Zoanthus* sp. (depicted in SEQ ID NO: 3, with an excitation wavelength of 493 nm and an emission wavelength of 505 nm or the protein depicted in SEQ ID NO: 4, synthetic sequence derived from *Aequorea victoria* (Jellyfish) with an excitation wavelength of 490 nm and an emission wavelength of 510 nm.

In a specific embodiment, the construct is SEQ ID NO: 5, that contains a *Triticum aestivum* HMWG promoter, a *Zoanthus* sp. FP protein and a *Arabidopsis thaliana* terminator (SEQ ID NO: 6).

As indicated above, the method is particularly adapted when the plant is an angiosperm, and in particular a *Graminae* (*Poaceae*). As exemplified below, the method is particularly adapted for maize or wheat seeds. barley, rice, oat, rye, and sorghum In particular, when used on wheat seeds, it may be favorable to soak the seeds before performing the method of the invention. Soaking the seeds prior to fluorescence detection may also be favorable for barley, rice, oat, rye, and sorghum seeds.

Indeed, in some case, one may observe a natural fluorescence of the wheat seed (in particular the envelope and the aleurone layer of the seed), that may be due (without being bound by this theory) to phenolic compounds that appear or get concentrated when the tissues and the seed dry out. Due to these compounds and self-fluorescence of the seed, it may prove difficult to clearly identify variations in the fluorescence intensity of the albumen due to the presence of different number of copies of the FP gene.

In order to reduce this endogenous fluorescence, one can soak the seed in water, or an aqueous solution for a few hours (such as for 4 to 12 hours, or even more) before performing the method herein described. Such rehydration of the seed will sensibly reduce self-fluorescence and hence allow detection of the specific fluorescence emitted by the FP protein and the ploidy level of the transgene. Thus, soaking the seeds before applying the method herein disclosed should increase the reliability of the results.

Once the seeds have been re-hydrated, they can be sowed or stored in the cold for as long as one month before sowing. They can also be dried again and stored for a long period of time. It was shown that the soaked grains still possess good germination capacity up to a month after soaking, which makes it possible to store the seeds for a month before sowing.

Once the ploidy of the transgene has been detected by the method herein described, it is possible to add a step of validating this determination by any method known in the art, such as PCR (directly on the seeds studied or at the next generation) and in particular qPCR, by segregation analysis on progeny.

The method herein described makes it possible to determiner and observe the fluorescence is that of the albumen, which is should contain 3 copies of the transgene (and hence of the genetically linked FP gene) in homozygous seeds. Indeed, in angiosperm, as seen above, the albumen shall contain two copies of the transgene of maternal origin and one copy of paternal origin.

If the detected fluorescence of the endosperm indicates the presence of two copies of the FP gene, it probably means that there was no fertilization by a transgenic pollen. The method described herein, and in particular using the FLUOStar system, makes it possible to differentiate the four classes of grain (WT, 1×, 2× and 3×) and can be followed by a validation by any method known in the art such as qPCR.

Thus, the invention also relates to a device (or apparatus) for reading the fluorescence emitted by seeds placed in wells of a plate, containing means for emitting an excitation wavelength onto said plate, and means for reading the fluorescence emitted by each well.

The means for emitting an excitation wavelength onto the plate comprises a radiation source which emits in a wavelength range of from 420 to 510 nm, preferably from 450 to 490 nm. It may be a laser.

The means for reading the fluorescence emitted by each well of the plate comprise a sensor which makes it possible to measure the radiation emitted by the seed in the well after excitation. This sensor may also determine the area (or areas) of the slide in which the fluorescence emission is performed. This sensor is regulated in such a way that it can determine the fluorescence emission in the wavelengths specified above, and centered around 550 nm. Examples of such means have been disclosed above. In one embodiment of the invention, this mean may be a fluorimeter.

Preferably, this device also comprises means for capturing images of each well of the plate.

These capture means may be a photographic apparatus which will be able to capture the image of each well of the plate emitting a fluorescence after excitation.

Preferably, these captured images are stored in a memory (present on the apparatus or remotely situated), in such a way that the user can gain access thereto via a computer means. These images can also be printed.

It may also comprise an automatic reader of a barcode or datamatrix code present on the plate, in order to identify the plate.

One can also analyze the seeds one at a time. This would be made with a seed distributor system on a conveyor with the seeds passing under one or more cameras that would take pictures of the seeds, and send the picture for it to be processed to determine the class of the seed (0×, 1×, 2× or 3×; or wild-type, heterozygous or homozygous) and an ejector system at the end of the conveyor in order to recover the seeds sorted in boxes corresponding to the determined class.

Thus, the device/apparatus may also be able to sort individual seeds depending on the level of fluorescence intensity that they emit after excitation at the proper wavelength.

Such device may comprise one or more of the following elements:
- a seed dispenser such as a distributor plate from a seed-drill, preferably with adjustable speed
- a conveyor belt preferably with adjustable speed to take into account the duration of image treatment and ensure that image from each seed can be obtained and treated.
- a trigger cell to take and synchronize picture of the seeds,
- a camera with adequate filters to measure the fluorescence (it may be monochromes)
- a color camera (preferably high resolution)
- a source of light to promote fluorescence of the seeds (such as a UV source or a laser)
- adequate filters to ensure that the adequate wavelength reach the seeds to make them fluoresce
- an ejector (such as a pressurized air ejector) to sort the seeds according to the fluorescence level, so as to eject the seeds in one out of three or four boxes corresponding to the expected classes (wild-type (one box), homozygous (one box), or heterozygous (one or two boxes)
- analyzer means (such as a computer with the adequate software) for determining the class of fluorescence of a given seed upon receipt of the information from the camera, and sending instructions to the ejector for to eject the seed in the bow corresponding to the determined class.

The invention thus particularly relates to a device for reading fluorescence emitted by seeds (and sorting seeds) comprising:
 a. a seed dispenser, in particular to individualize seeds on a conveyor belt
 b. a conveyor belt preferably with adjustable speed
 c. a source of light to promote fluorescence and adequate filters, this source of light being able, in particular, to light individualized seeds on the conveyor
 d. a camera with adequate filters to measure the level of fluorescence emitted by individualized seeds
 e. analyzer means for allocating the measured level of fluorescence in one of four classes of fluorescence (as determined with a software such as the statistical software Kmeans as disclosed in the examples, or the R suite, on control seeds)
 f. an ejector to eject and sort the seeds according to their appropriate fluorescence class.

This device is particularly interesting for reading fluorescence emitted by individual seeds from a seed lot. In this case, it is preferred that the control seeds are the seeds of this lot. The fluorescence is first measured on all seeds of the lot, making it possible to determine the four classes, and the seeds are then tested again and sorted according to the determined four classes.

The invention also relates to an automated and non-destructive process for determining the level of transgene zygosity in a seed, wherein said transgene is genetically linked to a gene coding for a fluorescent protein (FP protein) under the control of an endosperm specific-promoter, comprising the steps consisting in:
 a) subjecting the endosperm seed to a wavelength exciting the FP protein;
 b) measuring the intensity of the emitted fluorescence, in particular by capturing an image of the seed emitting the fluorescence;
 c) optionally storing the image obtained in b) such that the image is associated with the seed, in particular by associating a unique identifier for the seed and the image.

The method may also comprise the step of assigning a zyosity class to the seed (wild-type, heterozygous or homozygous for the transgene) depending on the level of intensity measured. This can be done by means of a computer software such as the one disclosed in the examples.

The method may also comprise the step of sorting the seeds according to their zygosity class.

In one embodiment, the four classes are calibrated within the software by self-learning on lots previously analyzed. In this embodiment, seeds can be sorted directly in one of the four classes.

In the preferred embodiment, though, and in order to reduce the variability inter-batches (i.e. for transgenic seeds originating from different transformation events), it is preferred to calibrate the four classes according to the fluorescence emitted from the various seeds of the same lots (i.e. originating from the same plant or from the same transformation event), and then to assign each seed to a class as designed. Calibration (design) of the four classes is performed with any appropriate statistical tool such as the Kmeans function described in the examples. The classes are thus designed on intra-lot seeds, and such calibration is performed again when a new lot/batch is run.

The invention also relates to a method for reading the fluorescence emitted by seeds (or determining fluorescence classes) comprising the steps of:
 a) Dispatching seeds from a seed lot [seeds from the same plant or from the same transgenic event] in wells of a plate,
 b) Placing the plate on a device containing means for emitting an excitation wavelength onto said plate, and means for reading the fluorescence emitted by each well,
 c) Measuring the fluorescence emitted by each seed upon excitation
 d) Analyzing emitted fluorescence for each seed with a statistic tool to create four classes according relative fluorescence.

The invention also relates to a method for reading the fluorescence emitted by seeds (or determining fluorescence classes) comprising the steps of:
a) Dispatching individual seeds under a belt moving through a device. (wherein the seeds are from a seed lot, i.e. come from the same plant or from the same transgenic event), wherein the device contains means for emitting an excitation wavelength onto said seed placed on a seed belt, and means for reading the fluorescence emitted by each seed,
b) Measuring the fluorescence emitted by each seed upon excitation
c) Analyzing emitted fluorescence for each seed with a statistic tool to create four classes according relative fluorescence of the seeds from a same seed lot.

The above two methods are preferably performed on seeds from angiosperm plants, and most specifically on seeds from graminae plants, and the fluorescence may be detected on the whole seed (embryo+endosperm) or on the endosperm only. In particular, the seeds are transgenic seeds, and the transgene is genetically linked to a gene coding for a fluorescent protein (FP protein) under the control of a promoter operative in the endosperm of the seed.

Even though the classes are created with a statistic tool, due to the medelian gene distribution, each class would correspond to a given transgene zygosity level in the endosperm (0×, 1×, 2×, 3×).

The invention thus relates to a method for sorting a transgenic angiosperm seed, wherein the transgene is genetically linked to a gene coding for a fluorescent protein (FP protein) under the control of a promoter operative in the endosperm of the seed, comprising the steps of
a) exposing the endosperm of the seed to a wavelength exciting the FP protein
b) measuring the fluorescence emitted by each seed upon excitation
c) allocating the measured level of fluorescence in one of the four classes of fluorescence, as determined by a method described above
d) sorting the seed according to its allocated class of fluorescence.

The following examples are meant to describe an aspect of invention, but shall not be limiting the invention.

EXAMPLES

Figure 1:
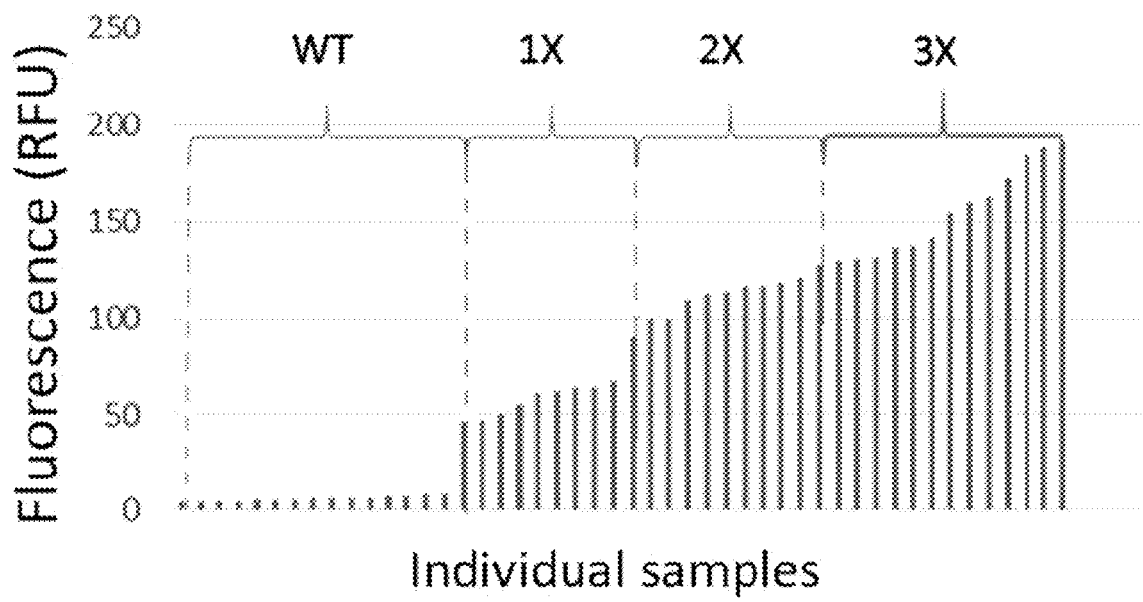
FIG. 1: Histograms representing the fluorescence (RFU, Relative Fluorescence Units) observed with Image J. Each bar corresponds to a specific individual, and they are sorted from the lowest to the highest fluorescence intensity. The four different classes (WT, 1×, 2×, 3×) are shown.

Example 1. Application to Maize 1-1—Genetic Modified Maize.

The seeds come from plants genetically transformed with *Agrobacterium tumefaciens* (Ishida et al., 1996), each construct (T-DNA) comprising:
One or more Genes Of Interest (GOI) under the control of suitable promoter;
A marker (selection) gene, under the control of a constitutive promoter, used to select the plants having integrated the transgene, such as an herbicide resistance gene, in particular the bar gene that confers resistance to Glufosinate, phosphinotricin and Bialaphos.
A reporter gene to obtain fluorescence in the endosperm (a ZsGreen encoding gene, as described above (SEQ ID NO: 3).), under the control of a promoter functional in the endosperm, in particular the HMWG promoter (SEQ ID NO: 2).

For the experiments the seed lots used come from a self-fertilization of regenerated transgenic plants. The transformation events have a molecular profile with one intact copy of the T-DNA. Genetically, there are 3 different genotypes in each seed lot with the following proportions: ¼ of wild grains (WT) or null segregant, ½ of heterozygous (HE) grains and ¼ of homozygous (HO) grains. Due to the double fertilization, the albumen of the grain can exist with four different number of transgenes: the genotype WT with no transgene, HE with 1 copy (1×) of the transgene when originating from the paternal zygote or 2 copies (2×) of the transgene when originating from the maternal zygote and 3 copies (3×) for the genotype HO with one 1 paternal and 2 maternal copies.

1-2—Visual Classification of ZsGreen Seeds.

96 lots of seeds were visually sorted by 3 different operators. The observations were made with a Leica MZ10 F fluorescence microscope equipped with the Leica EL6000 external light source. A magnification ×8 and excitation with a wavelength of 480 nm and a stopping filter at 510 nm were used (kit fluorescence GFP Plus).

The grains expressing the ZsGreen were separated into 2 fractions (1 low intensity fraction and 1 high intensity fraction).

For each of the 96 batches, 3 kernels from the high intensity FP fraction were sown and genotyping by quantitative PCR were done on corresponding plantlets. The results gave a rate of 63% of homozygous plantlets and 37% of hemizygous plantlets. This experiment shows that this visual sorting of seeds by the intensity level of the endosperm FP allows the identification of potentially 3× transgene copy endosperm. An average rate of 63% of 3× endosperm is contained in this high intensity FP fraction while only 33% of FP positive seeds contains 3× copies. This classification has been shown to be similar with the 3 different operators.

1-3—Classification of ZsGreen Seeds by Image J 48 maize caryopses are placed in wells of plates "NUNC 48" (THERMOSCIENTIFIC, Waltham, Mass., USA). The seeds are preferably stuck on the bottom of the wells to prevent seed movement, endosperm is on the upper face.

For observation of the fluorescence and acquisition of photos, the Leica MZ10 F modular stereo microscope is used with the Leica EL6000 external light source. High-definition pictures are taken with the Leica DFC420 C, a digital microscope camera with c-mount and with a 5 Mpixel CCD sensor.

The filters kits installed on the microscope are:
the kit Fluorescence GFP Plus (emission filter wavelength 480/40 nm; stop filter wavelength 510 nm)
the kit fluorescence GFP Plants (emission filter wavelength 470/40 nm; stop filter wavelength 525/50 nm) and
the filter nGreen (emission filter wavelength 490/20 nm; stop filter wavelength 530/20 nm), which is the one preferred and further used.

The camera is driven by the Leica Application Suite V3.3.0. This software makes it possible to adjust the exposition of the sensor to fluorescence in order to avoid saturation in the green light.

The pictures are stored for further analysis, with the suite Image J V 1.47, Open Source software available at http://imagej.updatestar.com. Using the function "Measure RGB" the average Green pixels intensity is determined on a 300×300 pixel area of the seed picture. These values are sorted in ascending order and entered in a histogram. Seeds are allocated into four class relative to their relative fluorescence intensity by a Kmeans function (see 2.6). The results for 48 seeds are illustrated in FIG. 1.

1-4—Classification of ZsGreen Seeds by Fluorimeter (Fluostar)

The same plates were used with a fluorimeter.

The FLUOstar OPTIMA Microplate Reader (BMG LABTECH, Ortenberg, Germany) is used to measure fluorescence at an excitation wavelength of 485 nm and an emission wavelength of 520 nm. This automat is controlled with the OPTIMA Control Software V2.20. Once measured, the data obtained are processed with the suite OPTIMA MARS Data Analysis V2.41. The automat is programed in order to avoid obtaining data with a maximum of 65 000 RFU (Relative Fluorescence Units).

Figure 2:
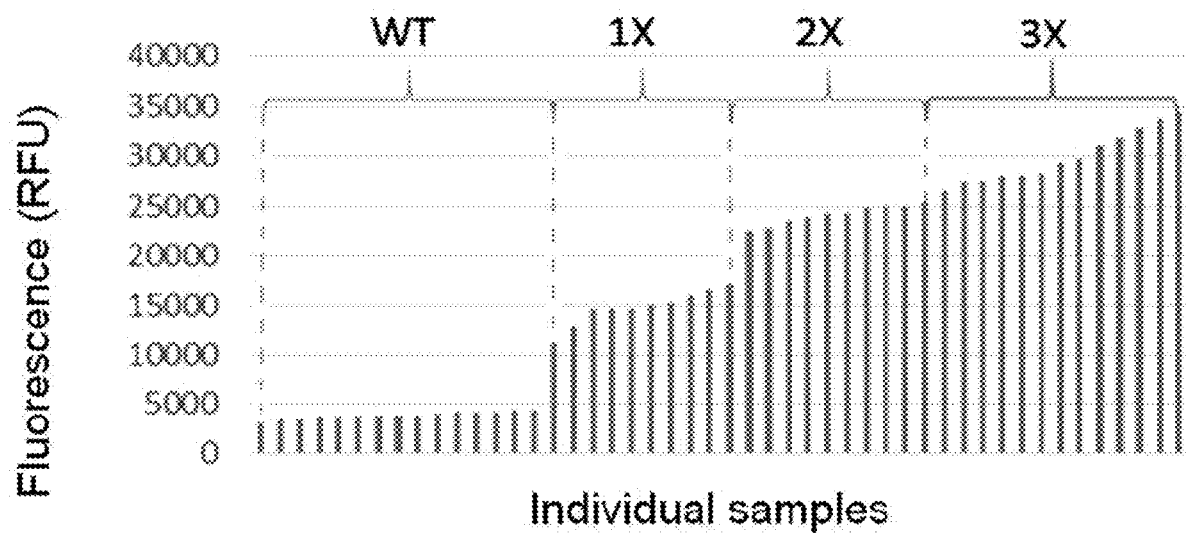
FIG. 2: Histograms representing the fluorescence (RFU) acquired with FLUOstar. Each bar corresponds to a specific individual, and they are sorted from the lowest to the highest fluorescence intensity. The four different classes (WT, 1×, 2×, 3×) are shown.

Each well of the plate was scanned by 80 consecutive flashes (SCAN protocol) distributed over a disk 10 mm in diameter centered on each well. An average of 80 values for each well is done. These values are sorted in ascending order and entered in a histogram. The results for 48 seeds are illustrated in FIG. 2.

This diagram shows that the fluorescence intensity of the grains does not increase continuously. It is possible to distinguish four levels by a Kmeans function (see 2.6).

1-5—Comparison of the Two Methods of Fluorescence Reading Image J and FLUOStar

Figure 3:
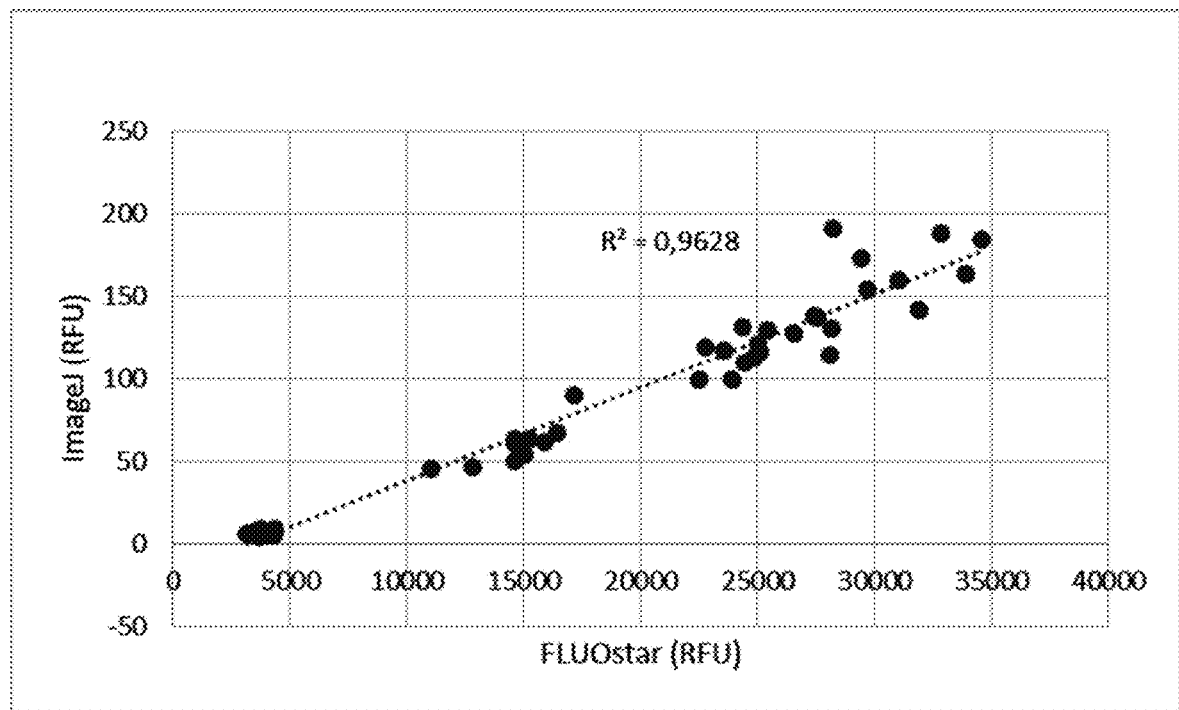
FIG. 3: Graph of the correlation between the measures obtained with Image J and the measures of the FLUOstar, SCAN protocol.

Correlation between fluorescence measurements obtained by Image J and FLUOstar method for the 48 seeds are shown in FIG. 3.

The $R^2$ (coefficient of determination) between the results obtained with the FLUOStar and the Image J software is of $R^2=0.9628$, indicating that any of the two tested fluorescence analysis software can be used with the same rate of accuracy.

1-6—Optimization of the Use of FLUOStar

Figure 4:
FIG. 4: Illustration of the principle of "orbital averaging". Distribution of the number of flashes (dark circles) depending of the diameter (light circle). a. illustration for 7 flashes, b. illustration for 16 flashes on a smaller diameter.

The FLUOstar proposes the "orbital averaging" measurement mode (FAST protocol), which measures the fluorescence emitted on the circumference of a circle centered on the well, the diameter of which having been pre-selected, and the maximum number of flashes depending on the selected diameter FIG. 4.

Figure 5:
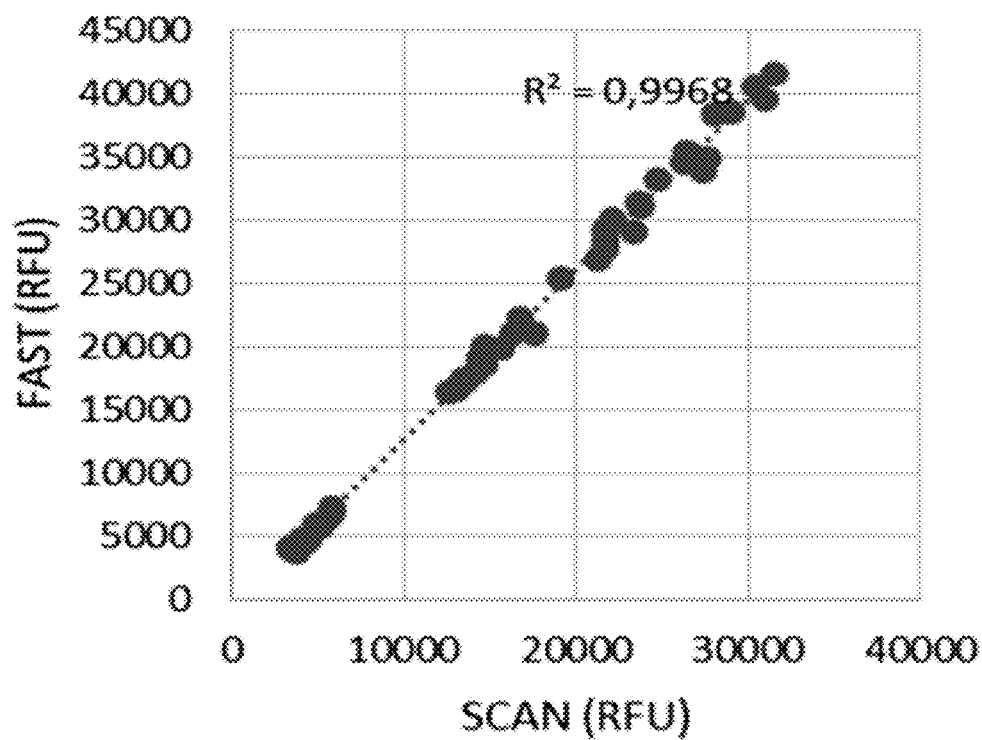
FIG. 5: Graph of the correlation of fluorescence measurement between the FAST protocol (diameter 5 mm, 12 flashes) and the SCAN protocol.

To identify the FAST protocol that is gives the best correlation with to the SCAN protocol (previous example), several diameters and number of flashes are tested (Ø 3 mm, 5 flashes); (Ø 3 mm, 3 flashes); (Ø 3 mm, 10 flashes); (Ø 4 mm, 5 flashes); (Ø 5 mm, 8 flashes); (Ø 5 mm, 12 flashes). These protocols require a measurement time of 30 to 40 seconds per plate. FIG. 5 shows the correlation between the FAST protocol Ø 5 mm, 12 flashes and the SCAN protocol. It is noted that the diameter influences the accuracy of the measurement. A diameter of 5 mm gives a best correlation with the SCAN protocol than a diameter of 3 or 4 mm.

The number of flashes per well has less influence, especially when the diameter is small (3 mm).

The protocol with Ø 5 mm and 12 flashes was selected, and gives similar results to the SCAN, in a shorter lapse of measure (4 times faster).

1-7—qPCR Validation of Zygoty Status Identified by Image J or the FLUOstar Method With the FLUOstar measurements the grains can be classified according to their fluorescence to predict their zygosity level with regards to the fluorescent protein and hence the transgene. To evaluate the reliability of this test, the results were confirmed by qPCR analysis on the plantlets germinated from these seeds.

Unlike caryopsis whose endosperm is triploid, the plantlets are diploid. It is therefore impossible to verify whether the endosperms are 1× or 2×, the two classes will leads to hemizygous plantlets with the molecular analysis.

For 4 independent seed lots, event 1 to 4, all 48 seeds measured by FLUOstar and classified as wild type (null segregant), homozygous for the transgene (3×) and heterozygous for the transgene (1× or 2×) were sown. The corresponding plantlets were analyzed by qPCR and classified into wild type, homozygous or heterozygous for the transgene. The table below shows the percentage of seeds with identical results between both methods.

TABLE 1 result concordance of FLUOstar classification on seeds and pPCR on resulting plantlets in percentage.

| | Null segregant | Heterozygous | Homozygous | Overall concordance |
|---|---|---|---|---|
| Event 1 | 100 | 94 | 67 | 88 |
| Event 2 | 100 | 85 | 86 | 89 |
| Event 3 | 100 | 100 | 90 | 97 |
| Event 4 | 100 | 96 | 60 | 94 |
| total | 100 | 93 | 76 | 92 |

A good correlation is obtained between the qPCR and FLUOstar results. Analysis by fluorimetry for the determination the zygosity on grains, gives better results than visual sorting (92% versus 63%).

1.8—Use of the Method for Phenotypic Evaluation of Maize Transgenic Events.

A construct containing a gene coding for a fluorescent protein under the control of an endosperm specific promoter, a selection marker and a gene of interest under the control of a suitable promoter is used for genetic transformation. Maize transgenic events were produced in tissue culture and seeds from the transgenic T0 plants harvested. After self-pollination of the T1 plants the segregation rate obtained from the seeds (with regards to the transgene) is 50% of heterozygous seeds, 25% homozygous and 25% wild type.

Submitting the seeds to appropriate light emission and measuring the emitted fluorescence with the FLUOStar method for example made possible to sort of seeds in four categories according to their endosperm zygosity level for the FP:
- no FP for the 25% wild type seeds.
- 1× of 2× in the endosperm for the 50% heterozygous seeds for the transgene.
- 3× for the 25% homozygous seeds for the transgene.

Figure 9:
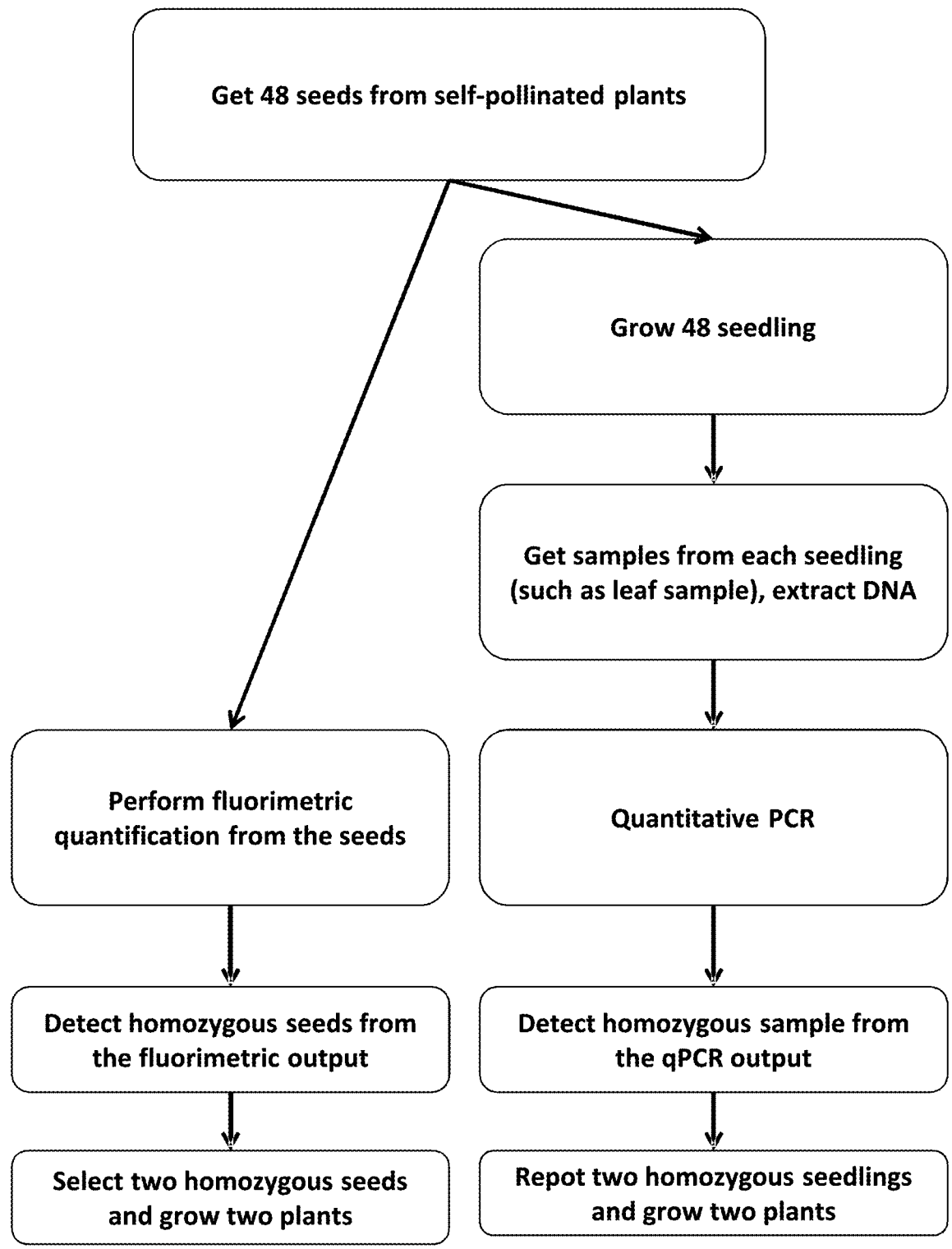
FIG. 9: Comparison of two methods for selecting homozygous seeds. Left: method herein described using the detection of the fluorescence in the embryo of seeds. Right: method widely used in the art, using quantitative PCR to detect homozigosity.

Only seeds from the last category are recovered and used in future development (sown and crossed with another variety to produce a hybrid progeny in order to perform phenotypic evaluation on the progeny). If a lot containing 48 seeds is analyzed, there are generally enough seeds in the last category (3×) to perform the selection scheme. This method is less time consuming than the regular step of sowing numerous seeds followed by sampling/screening of plantlets. The cost of zygosity determination is thus significantly reduced, the time necessary for sampling and doing the molecular analysis (qPCR) is saved as is the cost of the reagents (FIG. 9).

An experiment was performed on 288 independent events. For each event, 48 seeds were analyzed. From these 48 seeds of each event, the five seeds having the most important fluorescence value have been retained (from seed 1 to seed 5 by decreasing fluorescence level), sowed and the homozygosity of the plant was checked:
- on seedlings by Q-PCR (quantitative PCR; it is to be noted that this method gives non-conclusive results in 1% to 2.4% of cases).
- Or on the ears obtained from the plants grown from these seeds. If the initial seed is homozygous for the GFP, all seeds on the ear will be GFP positive; if the seed is heterozygous, the ear will be segregating (some seeds will be GFP positive and others no)

After analysis of the plants obtained from the sowed seeds, the result is as in Table 2. The success rate corresponds to the number of plants (issued from seed 1 to 5 for each of the 288 independent events) for which the grown plants were effectively homozygous.

TABLE 2

Percentage of homozygous plants, from all plants grown from the 5 seeds selected with the highest fluorescence level

| | Success rate |
|---|---|
| Seed 1 | 92.7% |
| Seed 2 | 92.4% |
| Seed 3 | 90.1% |
| Seed 4 | 88.1% |
| Seed 5 | 86.2% |

This table shows that the method makes it possible to select seeds with homozygous genotype with a very high level of success, and makes it possible to save a lot of time and resources.

In a routine protocol, only the two first seeds (seed with the highest detected fluorescence) can be selected as illustrated in FIG. 9. This protocol has been tested on a larger scale on 2444 events, and homozygous plants were recovered for 2216 events amounting to a success rate of 91.1%.

Example 2. Application to Wheat 2-1—Genetic Modified Wheat.

The seeds are obtained from plants genetically transformed with *Agrobacterium tumefaciens* (Ishida et al., 2015), each construct comprising:
- One or more Genes Of Interest (GOI) under the control of suitable promoter;
- A marker (selection) gene, under the control of a constitutive promoter, used to select the plants having integrated the transgene, such as an herbicide resistance gene, in particular the bar gene that confers resistance to Glufosinate, phosphinotricin, Bialaphos or the nptII selection marker conferring resistance to phosphinotricine.
- A reporter gene that allows fluorescence in the endosperm (a ZsGreen-encoding gene (SEQ ID NO: 3), under the control of a promoter functional in the endosperm, in particular the HMWG promoter (SEQ ID No: 2).

For the experiments the seed lots were obtained from a self-pollination of regenerated T0 plants.

2-2—Visual Classification of ZsGreen Seeds 20 lots of seeds were visually sorted. With the protocol described in example 1.2 and the nGreen filter.

Different levels of intensity were observed for seeds expressing ZsGreen. It was possible to separate the grains expressing ZsGreen from those not expressing ZsGreen. However they were sometimes difficult to differentiate due to endogenous background fluorescence in the seed coat.

After visual sorting and separation, grains were counted to perform a calculation of segregation. The data obtained is given in the following table:

TABLE 3 twenty seeds lots from independent transformation events sorted according the presence or absence of a fluorescent protein (FP).

| Events (seed lots) | Number of seeds | Percentage of seeds positive for FP | Percentage of seeds negative for FP |
|---|---|---|---|
| Event 1 | 64 | 75% | 25% |
| Event 2 | 53 | 72% | 28% |
| Event 3 | 41 | 76% | 24% |
| Event 4 | 63 | 60% | 40% |
| Event 5 | 189 | 71% | 29% |
| Event 6 | 115 | 78% | 22% |
| Event 7 | 99 | 77% | 23% |
| Event 8 | 43 | 79% | 21% |
| Event 9 | 235 | 77% | 23% |
| Event 10 | 348 | 64% | 36% |
| Event 11 | 116 | 82% | 18% |
| Event 12 | 64 | 77% | 23% |
| Event 13 | 109 | 74% | 26% |
| Event 14 | 84 | 75% | 25% |
| Event 15 | 100 | 73% | 27% |
| Event 16 | 75 | 71% | 29% |
| Event 17 | 32 | 56% | 44% |
| Event 18 | 37 | 62% | 38% |
| Event 19 | 269 | 62% | 38% |
| Event 20 | 94 | 50% | 27% |

The expected Mendelian segregation is ¾ FP+, ¼ FP− is obtained for most of the lots. It appears that it is possible to discriminate fluorescence-positive from fluorescence-negative grains, with sometimes hesitation to differentiate a wild-type seed from a weakly positive seed.

This observation also reveals a difference of intensity emitted by the fluorescence-positive grains, which seems to demonstrate that the fluorescence intensity may indicate the level of zygosity of the grain.

The seeds of each event were classified after visual evaluation in one of the following three classes:

Highly fluorescent grains (FP++)
Fluorescent grains (FP+), not considered highly fluorescent
Non-fluorescent grains (FP−)

TABLE 4 sorting of seeds for the event 20, into tree classes, absence of fluorescent protein, and presence of fluorescent protein with two level of intensity.

| Event | Nb seeds | FP− | FP+ | FP++ |
|---|---|---|---|---|
| Event 20 | 94 | 25 (27%) | 47 (50%) | 22 (23%) |

The proportions obtained confirm the Mendelian segregation of ¼ seeds homozygous (FP++), ¼ wild-type seeds (FP−) and ½ hemizygous seeds (FP+).

These observations indicate that the ZsGreen protein can be used as a marker of zygosity of the seed.

Figure 6:
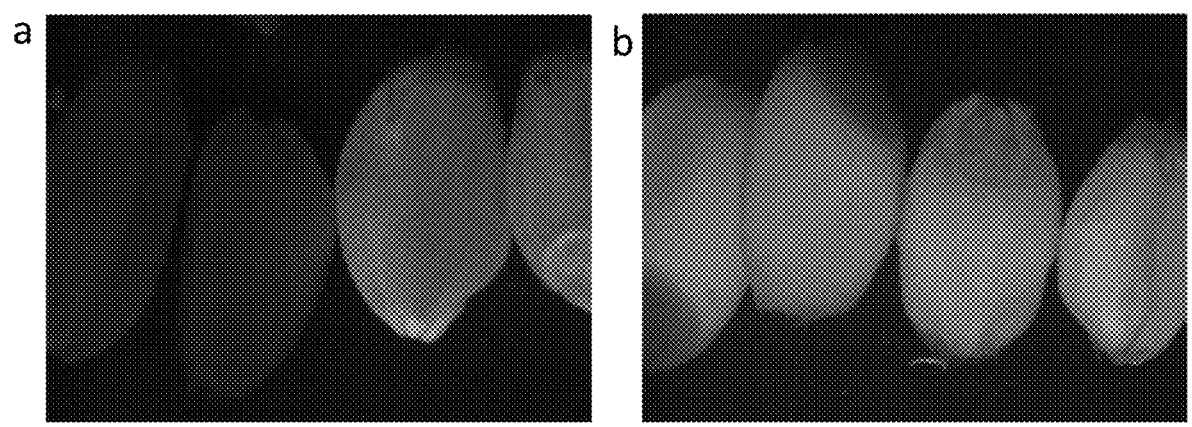
FIG. 6: a. comparison of the fluorescence observed on wild-type wheat seeds, soaked (left) or dry (right). b. comparison of the fluorescence observed on wheat seeds transformed with FP, soaked (left) or dry (right). One can see that there is a slight natural fluorescence for non-soaked seeds and that the level of fluorescence diminishes when the seeds have been soaked.

To improve the sorting, the seeds were imbibed in water at room temperature for a duration of 8 hours. After soaking, the seeds expressing ZsGreen and those not expressing ZsGreen, were more easily sorted visually (FIG. 6). Each picture shows four seeds two soaked seeds on the left and two dry seeds on the right, (a) wild type seeds and (b) fluorescent positive seeds.

2-3—Classification of ZsGreen Seeds by Fluorimeter (FLUOstar)

48 wheat caryopses from a seed lot were placed in wells of plates "NUNC 48" (THERMOSCIENTIFIC, Waltham, Mass., USA). The seeds were preferably stuck on the bottom of the wells to prevent seed movement. The round part of the endosperm was preferably placed facing upwards with the groove stuck to the bottom of plate.

FLUOstar OPTIMA Microplate Reader (BMG LABTECH, Ortenberg, Germany) was used to measure fluorescence at an excitation wavelength of 485 nm and an emission wavelength of 520 nm. This automat is controlled with the OPTIMA Control Software V2.20. Once measured, the data obtained were processed with the suite OPTIMA MARS Data Analysis V2.41.

The automat was programed in order to avoid obtaining data with a maximum of 65 000 RFU (Relative Fluorescence Units).

Each well of the plate was scanned by 10 consecutive flashes distributed over a disk 2 mm in diameter centered on each well. An average of 10 values for each well is done. These values are sorted in ascending order and entered in a histogram.

Figure 7:
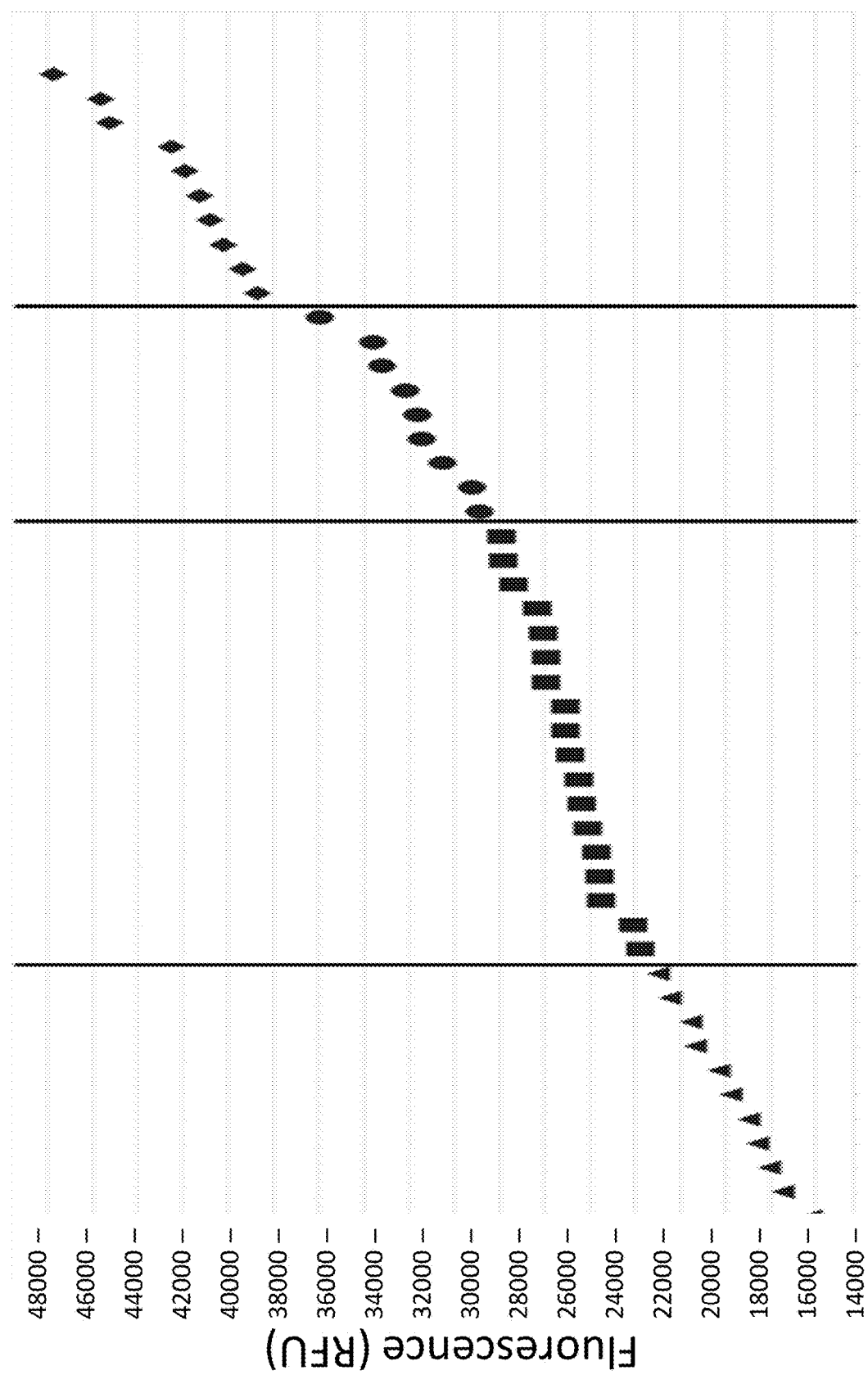
FIG. 7: Example of graph generated with the Kmeans function. The different classes are shown and separated by the vertical bars. 0×: triangles; 1×: squares; 2×: circles; 3×: diamonds. Each symbol corresponds to a specific individual. a, dry seeds; b. soaked seeds.
Figure 7:
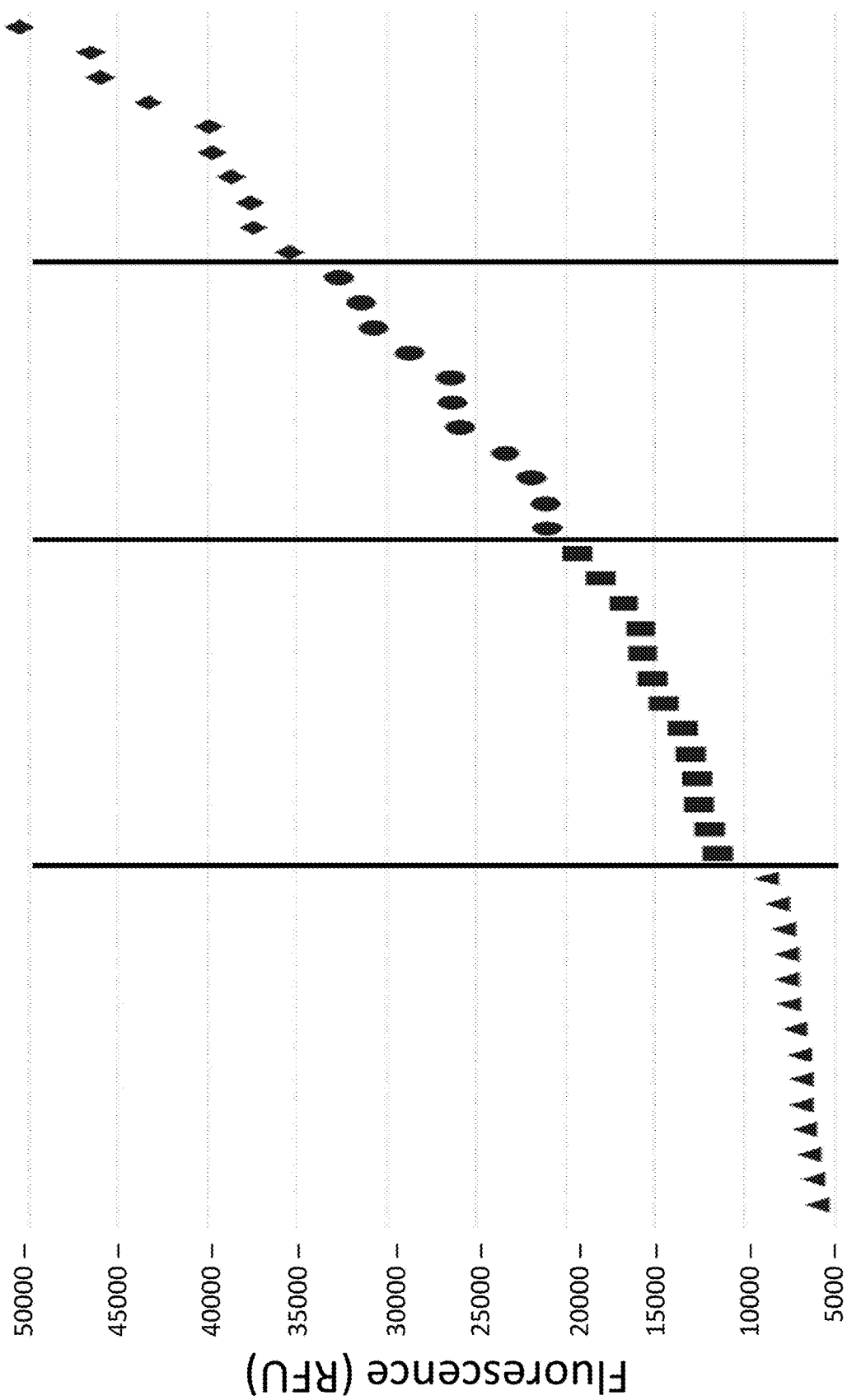

The measurements were made on dry seeds and then on imbibed seeds. The results for 48 seeds are illustrated in FIGS. 7 (a, dry seeds and b, imbibed seeds). The comparison of graphics shows a better separation of the classes with the imbibed seeds.

2.4 Soaking the Seeds

Visually, the soaked grains appear swelled, and the differences in fluorescence intensity seem easier to determine, in particular improves the detection of the negative (wild-type) grains, as it seems easier to visually detect positive grains. Fluorescence measurements were made on dry grains and on soaked grains. All events were assessed with the FLUOstar as dry grains and soaked seeds to obtain the two intensity values. All events were soaked directly in the microplate for 8 hours before another run with FLUOstar.

Figure 8:
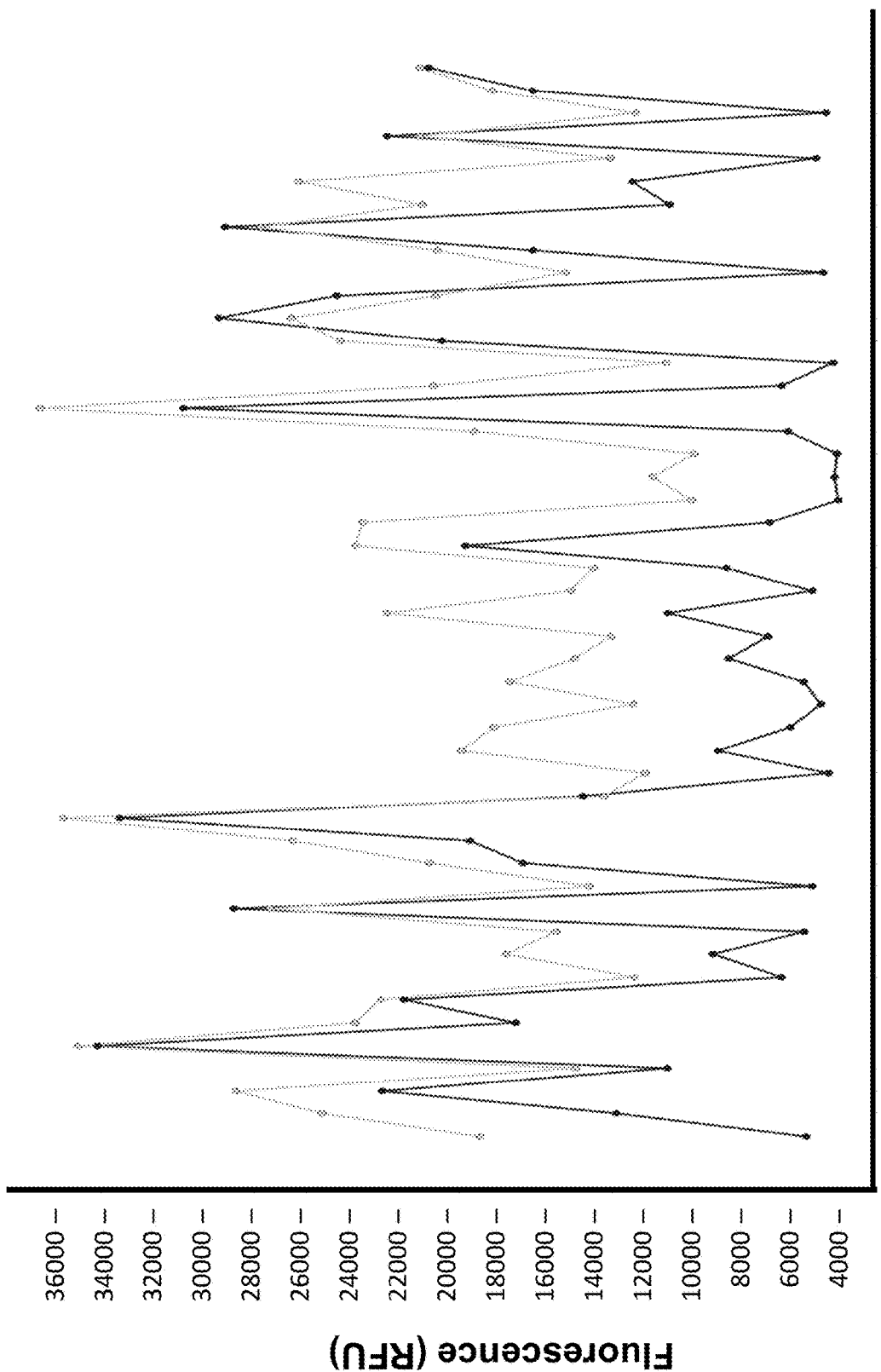
FIG. 8: Comparison of the fluorescence intensity observed for wheat seeds that have been soaked (darker line) or not (lighter line).

Soaking leads to lower overall intensity values, with a curve having a similar pattern than for dry grains (see FIG. 8). The interpretation of intensity values is quite similar.

Soaking the seeds provides better separation between classes, especially at the transition classes WT (wild-type) and 1× (hemizygous). Previously soaked wild grains seem to lose any fluorescent intensity, whereas there is a slight endogenous fluorescence in dry wild-type seeds.

2.5 Seed Orientation for Fluorimeter (FLUOstar) Measurement

For maize, the orientation of the seed is important (opposite side to the embryo that is measured). For wheat, the embryo representing a small part of the grain, the measurement can be made on any side yielding similar results.

2-6 Use of the Kmeans Function

The fluorescence intensity data in the Excel file are then exported to the R software to perform the Kmeans function.

This tool generates a matrix of each microplate with the 48 wells scanned by the FLUOstar and a graph of these 48 wells according to the increasing intensity of fluorescence.

The Kmeans function also allows dividing the data set in a number of classes defined by assessing the distance of one point to the average of the other points in its class.

The software was parametered as to provide 4 classes that are expected for the four zygosity levels (WT/1×/2×/3×). The classes are represented by different symbols (FIG. 1, 2, 7).

The Kmeans function also provides the identity of the four grains having the highest fluorescence intensity.

2. 7 qPCR Validation of Zygosity Status Identified by the Fluorimeter Method

With the FLUOstar measurements the grains can be classified according to their fluorescence to predict their zygosity level. To evaluate the reliability of this test the results were confirmed by qPCR analysis on the plantlets germinated from these seeds.

Unlike caryopsis whose albumen is triploid, the plantlets are diploid. It is therefore impossible to verify whether the grains are 1× or 2×, the two classes will be detected hemizygous with the molecular analysis.

In a first experiment dry seeds were analyzed: For 4 independent events, 48 seeds were measured by FLUOstar and then sown. The germinated seeds were sampled and analyzed by qPCR. The table below shows the percentage of seeds with identical results between both methods per event:

TABLE 5 result of concordance of FLUOstar classification of dry seeds and pPCR for the corresponding plantlets.

| | Null segregant (%) | Heterozygous (%) | Homozygous (%) | Overall concordance (%) |
|---|---|---|---|---|
| Event 3 | 57 | 73 | 33.5 | 58 |
| Event 6 | 87.5 | 71.5 | 44.5 | 68 |
| Event 10 | 100 | 84 | 70 | 85 |
| Event 13 | 91.5 | 82.6 | 60 | 80 |
| total | 87 | 78.5 | 52.5 | 75 |

In a second experiment, imbibed seeds were analyzed. For 2 events, 48 seeds were soaked in water at room temperature for a duration of 8 hours before the fluorescence was measured by FLUOstar and then sown. The table below shows the percentage of seeds with identical results between both methods per event:

TABLE 6 result of concordance of FLUOstar classification on imbibed seeds and pPCR for the corresponding plantlets.

|  | Null segregant (%) | Heterozygous (%) | Homozygous (%) | Overall concordance (%) |
|---|---|---|---|---|
| Event 10 | 100 | 100 | 90 | 98 |
| Event 13 | 100 | 95.5 | 50 | 87 |
| total | 100 | 98 | 70 | 92 |

The comparison of the reliability of the results obtained on the dry seeds and the soaked seeds shows that both techniques give good results. However, the measurement on imbibed seeds is more preferred.

2.8 Comparison of the Method Herein Disclosed and the Method Usually Performed for Detecting Homozygous Seeds (qPCR on Leaf Samples or Half-Seeds)

The method as disclosed above makes it possible to identify homozygous seeds in half the time needed using the prior methods, for a much lower cost (essentially null) where the other qPCR methods have, at least, the cost of reagents.

2.9 Use of the Method for Phenotypic Evaluation of Transgenic Events.

The method can be used in the same way as described for maize for the phenotypic evaluation of transgenic events in wheat. On a larger scale experiment of 135 events, homozygous plants were recovered for 127 events: success rate is of 94.1%.

V. Conclusion

In conclusion, this demonstrates that one can use the fluorescent reporter genes widely used in biotechnology to detect the state of zygosity of a transgene in a plant breeding system, directly on seeds, by detection of a fluorescence of a specific part of the seeds that is different from the embryo (detection in the endosperm).

The method is also very applicable to angiosperm plants (as herein exemplified on maize and wheat) and also allows determine whether the transgene, in hemizygous plants, comes from the maternal or paternal side.

There is a real advantage for the technique herein described, in time of preparation of samples (no need to sow and wait for plantlets to analyze, no need to prepare DNA for a large number of samples) and cost.

REFERENCES

Carlson A., J Letarte, J Chen, K Kasha—Plant cell reports, 2001, 20: 331-337; "Visual screening of microspore-derived transgenic barley (*Hordeum vulgare L.*) with green-fluorescent protein";

CHYTILOVA E, MACAS J, GALBRAITH D. W (1999) Green fluorescent protein targeted to the nucleus, a transgenic phenotype useful for studies in plant biology. Annals of Botany, 83, 645-654.

Christensen et al, Plant Mol. Biol. 18 (4), 675-689 (1992) Maize polyubiquitin genes: structure, thermal perturbation of expression and transcript splicing, and promoter activity following transfer to protoplasts by electroporation Fiume, E., Christou, P., Giani, S. et al. Planta (2004) 218: 693.; Introns are key regulatory elements of rice tubulin expression.

HALFHILL M, MILLWOOD R, STEWART C. N, JR (2004) Green Fluorescent Protein Quantification in Whole Plants. In: PEÑA, L. (ed.) Transgenic Plants: Methods and Protocols. Humana Press.

Halford et al 1989 (Plant Science 62, 207-16). Functional analysis of the upstream regions of a silent and an expressed member of a family of wheat seed protein genes in transgenic tobacco;

Hensel G, D M Floss, E Arcalis, M Sack, S Melnik, F. Altmann, T. Rutten, J. Kumlehn, E Stoger and U. Conrad PLOS ONE, october 2015 "Transgenic Production of an Anti HIV Antibody in the Barley Endosperm».

HRAŠKA M, RAKOUSKY'S, ČURN V (2006) Green fluorescent protein as a vital marker for non-destructive detection of transformation events in transgenic plants. Plant Cell, Tissue and Organ Culture, 86, 303-318.

HU W, CHENG C. L (1995). Expression of *Aequorea* green fluorescent protein in plant cells. FEBS Letters, 369, 331-334.

ISHIDA Y, TSUNASHIMA M, HIEI Y, KOMARI T (2015) Wheat (*Triticum aestivum L.*) Transformation Using Immature Embryos. Methods in molecular biology, 1223, 189-198.

LAMACCHIA C, SHEWRY P. R, DI FONZO N, FORSYTH J. L, HARRIS N, LAZZERI P. A, NAPIER J. A., HALFORD N. G, BARCELO P (2001) Endosperm-specific activity of a storage protein gene promoter in transgenic wheat seed. Journal of Experimental Botany, 52, 243-250.

MATZ M. V, FRADKOV A. F, LABAS Y. A, SAVITSKY A. P, ZARAISKY A. G, MARKELOV M. L, LUKYANOV S. A (1999) Fluorescent proteins from nonbioluminescent *Anthozoa* species. Nat Biotechnol 17, 969-973

McElroy et al 1990, Plant Cell 2:163; Isolation of an efficient actin promoter for use in rice transformation.

MOLINIER J, HIMBER C, HAHNE G, (2000) Use of green fluorescent protein for detection of transformed shoots and homozygous offspring. Plant Cell Reports, 19, 219-223.

NIELSEN, K., OLSEN, O. & OLIVER, R. 1999. A transient expression system to assay putative antifungal genes on powdery mildew infected barley leaves. Physiological and Molecular Plant Pathology, 54, 1-12.

NIWA Y, HIRANO T, YOSHIMOTO K, SHIMIZU M, KOBAYASHI H (1999) Non-invasive quantitative detection and applications of non-toxic, S65T-type green fluorescent protein in living plants. The Plant Journal, 18, 455-463.

Odell et al, Nature. 1985 313: 810-812 Identification of DNA sequences required for activity of the cauliflower mosaic virus 35S promoter;

RADEMACHER T., M SACK, E ARCALIS, J. Stadlmann, S. Balzer, F. Altmann, H. Quendler, G. Stiegler, R. Kunert, R. Fischer and E. Stoger, Plant biotechnology Journal (2008) 6, PP. 189-201; "Recombinant antibody 2G12 produced in maize endosperm efficiently neutralizes HIV-1 and contains predominantly single-GlcNAc N-glycans»;

RICHARDS H. A, HALFHILL M. D, MILLWOOD R. J, STEWART C. N (2003) Quantitative GFP fluorescence as an indicator of recombinant protein synthesis in transgenic plants. Plant Cell Reports, 22, 117-121.

Russel and Fromm Transgenic Res. 1997 March; 6(2):157-68. Tissue-specific expression in transgenic maize of four endosperm promoters from maize and rice. Shimada T L, T Shimada, I Hara☐Nishimura—The Plant Journal, 2010 "A rapid and non destructive screenable marker, FAST, for identifying transformed seeds of Arabidopsis thaliana";

Shimada T L, Y Ogawa, T Shimada and I Hara-Nishimura, Plant Signaling & Behavior 6:10 1454-1456, Octobre 2011; "A non-destructive screenable marker, OsFAST, for identifying transgenic rice seeds";

SHIMOMURA O (1979) Structure of the chromophore of Aequorea green fluorescent protein. FEBS Letters, 104, 220-222.

STEWART C. N, JR (2001) The utility of green fluorescent protein in transgenic plants. Plant Cell Reports, 20, 376-382.

THOMAS M. S, FLAVELL R. B (1990) Identification of an Enhancer Element for the Endosperm-Specific Expression of High Molecular Weight Glutenin. The Plant Cell, Vol. 2, 1171-1180.

Vain, P., Finer, K. R., Engler, D. E. et al. Plant Cell Reports (1996) 15: 489. Intron-mediated enhancement of gene expression in maize (Zea mays L.) and bluegrass (Poa pratensis L.)

Verdaguer B, de Kochko A, Beachy R N, Fauquet C. Isolation and Expression in Transgenic Tobacco and Rice Plants, of the Cassava Vein Mosaic Virus (CVMV) Promoter. Plant Mol Biol. 1996 September; 31(6):1129-39;

WENCK A, PUGIEUX C, TURNER M, DUNN M, STACY C, TIOZZO A, DUNDER E, GRINSVEN E, KHAN R, SIGAREVA M, WANG W. C, REED J, DRAYTON P, OLIVER D, TRAFFORD H, LEGRIS G, RUSHTON H, TAYAB S, LAUNIS K, CHANG Y. F, CHEN D. F, MELCHERS L (2003) Reef-coral proteins as visual, non-destructive reporters for plant transformation. Plant Cell Reports, 22,244-251.

YU W C in MOLECULAR BREEDING, 36(1) (2016). A green fluorescent protein-engineered haploid inducer line facilitates haploid mutant screens and doubled haploid breeding in maize

The invention claimed is:

1. A method for determining a level of transgene zygosity in a *poaceae* seed, the method comprising: providing a *poaceae* seed comprising a transgene that is genetically linked to a gene coding for a fluorescent protein (FP protein) under the control of a promoter operative in endosperm of the seed; exposing the endosperm of the seed to a wavelength exciting the FP protein; and measuring intensity of fluorescence emitted by the endosperm,
wherein the intensity of fluorescence emitted by the endosperm of the seed is further compared to intensity of fluorescence measured for individual seeds from a batch of seeds, wherein the batch of seeds is from the same plant or from the same transgenic event as the seed, wherein four classes (0×, 1×, 2×or 3×) of transgene zygosity levels are determined based on relative fluorescence intensity of the seeds of the batch.

2. The method of claim 1, wherein the intensity of fluorescence emitted by the endosperm of the seed is calculated after processing an image of the seed in a computer.

3. The method of claim 1, wherein the promoter is selected from the group consisting of HMWG promoter, maize gamma Zein promoter, CaMV35S promoter, rice actin promoter, maize polyubiquitin promoter, rice tubulin promoter, and CsVMV promoter.

4. The method of claim 1, wherein the seed has been soaked before being exposed to the wavelength exciting the FP protein.

5. The method of claim 4, wherein the soaking has been performed for a duration between 4 and 12 hours.

6. The method of claim 1, further comprising performing a PCR to validate ploidy of the transgene.

7. The method of claim 1, wherein the seed is a maize or a wheat seed.

8. A method for reading fluorescence emitted by transgenic *poaceae* seeds, the method comprising:
   a) providing a *poaceae* seed comprising a transgene that is genetically linked to a gene coding for a fluorescent protein (FP protein) under the control of a promoter operative in endosperm of the seed;
   b) dispatching seeds from a seed lot into wells of a plate;
   c) placing the plate on a device and exposing the plate to an excitation wavelength;
   d) measuring fluorescence emitted by each seed upon excitation; and
   e) analyzing fluorescence emitted by each seed with a statistic tool to create four classes according to relative fluorescence intensity of the seeds.

9. A method for reading fluorescence emitted by transgenic *poaceae* seeds, the method comprising:
   a) providing a *poaceae* seed comprising a transgene that is genetically linked to a gene coding for a fluorescent protein (FP protein) under the control of a promoter operative in endosperm of the seed;
   b) dispatching individual seeds onto a belt moving through a device and exposing the seeds on the belt to an excitation wavelength;
   c) measuring the fluorescence emitted by each seed upon excitation; and
   d) analyzing the fluorescence emitted by each seed with a statistic tool to create four classes according to relative fluorescence intensity of the seeds.

10. A method for sorting a transgenic *poaceae* seed, the method comprising:
    a) providing a *poaceae* seed comprising a transgene that is genetically linked to a gene coding for a fluorescent protein (FP protein) under the control of a promoter operative in endosperm of the seed;
    b) exposing the endosperm of the seed to a wavelength exciting the FP protein;
    c) measuring fluorescence emitted by each seed upon excitation;
    d) allocating a measurement of the fluorescence emitted by each seed to one of four classes of fluorescence intensity, as determined in claim 8; and
    e) sorting the seed according to its allocated class of fluorescence intensity.

11. A method for sorting a transgenic *poaceae* seed, the method comprising:
    a) providing a *poaceae* seed comprising a transgene that is genetically linked to a gene coding for a fluorescent protein (FP protein) under the control of a promoter operative in endosperm of the seed;
    b) exposing the endosperm of the seed to a wavelength exciting the FP protein;
    c) measuring fluorescence emitted by each seed upon excitation;
    d) allocating a measurement of the fluorescence emitted by each seed to one of four classes of fluorescence intensity, as determined in claim 9; and
    e) sorting the seed according to its allocated class of fluorescence intensity.

12. The method of claim 6, wherein the PCR is qPCR.

* * * * *